United States Patent [19]

Takada et al.

[11] Patent Number: 6,117,455
[45] Date of Patent: Sep. 12, 2000

[54] SUSTAINED-RELEASE MICROCAPSULE OF AMORPHOUS WATER-SOLUBLE PHARMACEUTICAL ACTIVE AGENT

[75] Inventors: Shigeyuki Takada, Kobe; Tomofumi Kurokawa, Hyogo-ken; Susumu Iwasa, Tsuzuki-gun, all of Japan

[73] Assignee: Takeda Chemical Industries, Ltd., Osaka, Japan

[21] Appl. No.: 08/535,386

[22] Filed: Sep. 28, 1995

[30] Foreign Application Priority Data

Sep. 30, 1994 [JP] Japan .................................. 6-236846

[51] Int. Cl.$^7$ .............................. A61K 9/50; A61F 2/00; A61F 13/00; A61F 9/02
[52] U.S. Cl. .......................... 424/501; 424/426; 424/433; 424/434; 424/436; 424/464; 424/499
[58] Field of Search .................................. 424/426, 451, 424/489, 50 L, 499, 433, 434, 436, 464

[56] References Cited

U.S. PATENT DOCUMENTS

| | | | |
|---|---|---|---|
| 3,853,837 | 12/1974 | Fujino et al. | 260/112.5 LH |
| 3,972,859 | 8/1976 | Fujino et al. | 260/112.5 LH |
| 4,008,209 | 2/1977 | Fujino et al. | 260/112.5 LH |
| 4,086,219 | 4/1978 | Wittle | 260/112.5 LH |
| 4,087,390 | 5/1978 | Shields | 260/8 |
| 4,093,574 | 6/1978 | Shields | 260/8 |
| 4,100,117 | 7/1978 | Shields | 260/8 |
| 4,124,577 | 11/1978 | Tinney et al. | 260/112.5 LH |
| 4,229,438 | 10/1980 | Fujino et al. | 424/177 |
| 4,253,997 | 3/1981 | Sarantakis | 260/8 |
| 4,253,998 | 3/1981 | Sarantakis | 260/8 |
| 4,277,394 | 7/1981 | Fujino et al. | 260/112.5 R |
| 4,317,815 | 3/1982 | Coy et al. | 424/177 |
| 4,954,298 | 9/1990 | Yamamoto et al. | 264/416 |
| 5,330,767 | 7/1994 | Yamamoto et al. | 424/497 |
| 5,622,657 | 4/1997 | Takada et al. | 264/432 |

FOREIGN PATENT DOCUMENTS

| | | |
|---|---|---|
| 0031567 | 7/1981 | European Pat. Off. . |
| 0325199 | 7/1989 | European Pat. Off. . |
| 0350246 | 1/1990 | European Pat. Off. . |
| 0357061 | 3/1990 | European Pat. Off. . |
| 0359036 | 3/1990 | European Pat. Off. . |
| 0386667 | 9/1990 | European Pat. Off. . |
| 0415294 | 3/1991 | European Pat. Off. . |
| 0477885 | 4/1992 | European Pat. Off. . |

(List continued on next page.)

OTHER PUBLICATIONS

American Association for the Advancement of Science, J. Folkman et al., Aug. 1983, pp. 719–725, "Angiogenesis Inhibition and Tumor Regression Caused by Heparin or a Heparin Fragment in the Presence of Cortisone".

Journal of Pharmaceutical Sciences, G. Spenlehauer et al., vol. 75, No. 8, Aug. 1986, "Formation and Characterization of Cisplatin Loaded Poly(d,i–Lactide) Microspheres for Chemoembolization".

Proceedings of the National Academy of Sciences, T. W. Redding and A. V. Schally, vol. 78, No. 10, pp. 6509–6512, Oct. 1981, "Inhibition of prostate tumor growth in two rat models by chronic administration of D–Trp6 analogue of luteinizing hormone–releasing hormone".

Endocrinology, vol. 93, No. 6, Dec. 1973, Geoffrey W. Tregear et al., "Bovine Parathyroid Hormone: Minimum Chain Length of Synthetic Peptide Required for Biological Activity".

*Primary Examiner*—Thurman K. Page
*Assistant Examiner*—Susan Tran
*Attorney, Agent, or Firm*—Fitzpatrick, Cella, Harper & Scinto

[57] ABSTRACT

A sustained-release microcapsule contains an amorphous water-soluble pharmaceutical agent having a particle size of from 1 nm–10 μm and a polymer. The microcapsule is produced by dispersing, in an aqueous phase, a dispersion of from 0.001–90% (w/w) of an amorphous water-soluble pharmaceutical agent in a solution of a polymer having a wt. avg. molecular weight of 2,000–800,000 in an organic solvent to prepare an s/o/w emulsion and subjecting the emulsion to in-water drying.

42 Claims, 1 Drawing Sheet

FOREIGN PATENT DOCUMENTS

| | | |
|---|---|---|
| 0481732 | 4/1992 | European Pat. Off. . |
| 0510662 | 10/1992 | European Pat. Off. . |
| 0251476 | 3/1993 | European Pat. Off. . |
| 50-121273 | 9/1975 | Japan . |
| 52-116465 | 9/1977 | Japan . |
| 57-118512 | 7/1982 | Japan . |
| 61-28521 | 2/1986 | Japan . |
| 4247034 | 9/1992 | Japan . |
| 5-32696 | 2/1993 | Japan . |
| 1423082 | 1/1976 | United Kingdom . |
| 13595 | 9/1991 | WIPO . |
| 91/00753 | 1/1992 | WIPO . |
| 11009 | 4/1995 | WIPO . |
| 33982 | 10/1996 | WIPO . |

SUSTAINED-RELEASE MICROCAPSULE OF AMORPHOUS WATER-SOLUBLE PHARMACEUTICAL ACTIVE AGENT

FIELD OF THE INVENTION

The present invention relates to a microcapsule containing an amorphous water-soluble physiologically active substance. The present invention also relates to a process for producing it.

BACKGROUND OF THE INVENTION

JP-A 57-118512 discloses a process for producing sustained-release microcapsules of a water-soluble drug which comprises encapsulating the drug by coacervation phase separation. This process has the following disadvantages: (1) the water-soluble drug is leaked out to the outer aqueous phase, and the drug entrapment ratio decreases, and it is difficult to obtain microcapsules having a high drug content, and (2) the resulting microcapsules have many pores and cause a large initial drug release. Journal of Pharmaceutical Science Vol. 75, No. 8, p. 750–755 (1986) discloses a process for producing microspheres which comprises preparing an s/o/w type emulsion from a dispersion of micronized dry powder of cisplatin in a poly(dl-lactide) solution and subjecting the emulsion to an in-water drying process. However, this literature fails to teach or suggest amorphous cisplatin or sustained-release of the drug over a long period.

OBJECTS OF THE INVENTION

The main object of the present invention is to provide a sustained-release microcapsule that has a high entrapment of a water-soluble drug and causes a small initial release.

Another object of the present invention is to provide a process for producing the above microcapsule.

These objects as well as other objects and advantages of the present invention will become apparent to those skilled in the art from the following description with reference to the accompany drawing.

SUMMARY OF THE INVENTION

The present inventors have intensively studied to achieve the above objectives. As a result, it has been found that a microcapsule comprising an amorphous water-soluble physiologically active substance and a polymer has a high entrapment of the physiologically active substance and causes a small initial release of the physiologically active substance. After further studies based on this finding, the present invention has been accomplished.

The present invention provides a microcapsule comprising an amorphous water-soluble physiologically active substance and a polymer.

The present invention also provides a microcapsule which is obtainable by dispersing in an aqueous phase a dispersion of an amorphous water-soluble physiologically active substance in a solution of a polymer in an organic solvent to prepare an s/o/w type emulsion and subjecting the emulsion to in-water drying.

The present invention also provides a process for producing a microcapsule, which comprises dispersing in an aqueous phase a dispersion of an amorphous water-soluble physiologically active substance in a solution of a polymer in an organic solvent to prepare an s/o/w type emulsion and subjecting the emulsion to in-water drying.

DETAILED DESCRIPTION OF THE INVENTION

Figure 1:
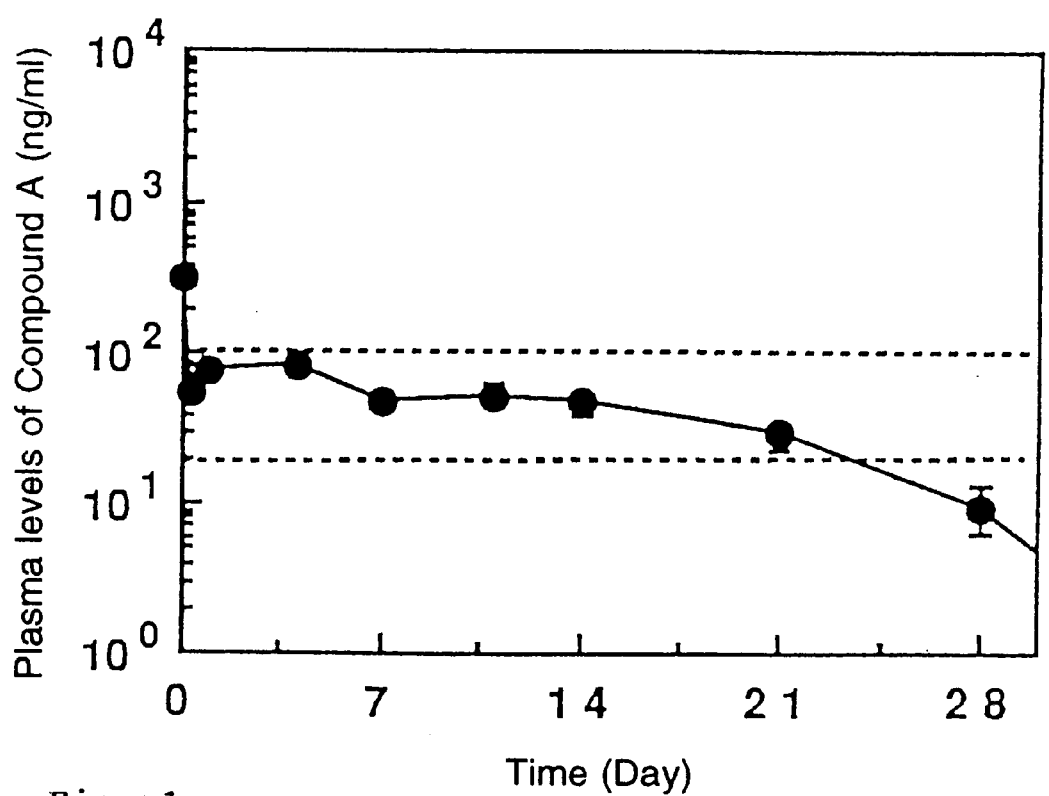
FIG. 1 is a graph showing the time-course changes of the plasma levels of (S)-4-[(4-amidinobenzoyl)glycyl]-3-methoxy-carbonylmethyl-2-oxopiperazine-1-acetic acid (abbreviated herein as Compound A) after subcutaneous administration of the Compound A—containing microcapsules (20 mg/kg) to rats. The plasma level of Compound A (ng/ml) is plotted as ordinate and the time (day) after the administration as abscissa.

The abbreviations of amino acids, peptides, protecting groups, etc., used herein are based on those established by IUPAC-IUB Commission on Biochemical Nomenclature or those commonly used in the art. When optical isomers of amino acids are present, the amino acids indicate L-isomers unless otherwise indicated.

The term "microcapsule" used herein is intended to include microspheres, microcapsules, microparticles, nanoparticles, nanospheres and nanocapsules.

The term "s/o/w type emulsion" used herein means a solid/oil/water (solid-in-oil-in-water) type emulsion. The "s" phase means a solid phase and is intended to include microparticles and aqueous phases in the form of a gel.

The present invention makes it possible to prepare a sustained-release microcapsule that contains a high content of a water-soluble physiologically active substance and causes a small initial release of the physiologically active substance.

The amorphous physiologically active substance used in the present invention is soluble in water. The term "soluble in water" or "water-soluble" means that the water-solubility of the physiologically active substance is generally not less than about 1 g, preferably not less than about 3 g, more preferably not less than about 5 g, per 100 ml of water at 20° C. Preferably, the physiologically active substance is readily soluble in water. The term "readily soluble in water" means that the water-solubility of the physiologically active substance is not less than about 5 g, preferably not less than about 10 g, per 100 ml of water at 20° C.

The physiologically active substance is not specifically limited so long as it is amorphous and water-soluble. Preferably, the physiologically active substance is an acidic or neutral substance.

Examples of the physiologically active substances include peptide compounds having biological activity, and other compounds used for drugs, such as antibiotics, antifungal agents, antilipidemic agents, drugs for circulatory systems, anti-platelet aggregation agents, antitumor agents, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive diuretics, antidiabetic agents, anticoagulants, hemostatics, antituberculous agents, hormone preparations, narcotic antagonists, bone resorption inhibitors, angiogenesis inhibitors, etc.

In particular, peptide compounds which are composed of two or more amino acids are preferred. The peptide compounds include proteins, polypeptides, derivatives thereof, and compounds having peptide-like structures. Preferably, these compounds have molecular weights of about 200 to 20,000. The present invention is particularly useful for peptide compounds that require long-term administration.

Examples of the peptide compounds include compounds having luteinizing hormone-releasing hormone (LH-RH) activity, such as LH-RH and its derivative of the formula (I):

(Pyr)Glu-R$_1$-Trp-Ser-R$_2$-R$_3$-R$_4$-Arg-Pro-R$_5$     (I)

wherein R$_1$ is His, Tyr, Trp or p-NH$_2$-Phe; R$_2$ is Tyr or Phe; R$_3$ is Gly or a D-amino acid residue; R4 is Leu, Ile or Nle; R$_5$ is Gly-NH-R$_6$ or NH-R$_6$ in which R$_6$ is H or lower alkyl optionally substituted with hydroxy, or salts thereof disclosed in U.S. Pat. Nos. 3,853,837, 4,008,209, 3,972,859; G.B. Patent No. 1,423,083; Proc. Nat. Acad. Sci. U.S.A., vol. 78, pp. 6509–6512 (1981).

The D-amino acid residues represented by R$_3$ in the above formula (I) include, for example, α-D-amino acids having 2 to 9 carbon atoms (e.g., D-Leu, Ile, Nle, Val, Nval, Abu, Phe, Phg, Ser, Thr, Met, Ala, Trp, α-Aibu). These residues may have appropriate protecting groups (e.g., t-butyl, t-butoxy, t-butoxycarbonyl) that are conventionally used for peptide synthesis. The lower alkyl groups represented by R$^6$ include, for example, alkyl groups having 1 to 6 carbon atoms, such as methyl, ethyl, propyl, butyl, etc.

Acid salts and metal complexes of the peptide of the formula (I) can also be used in the same manner as in the peptide of the formula (I).

The preferred peptide of the formula (I) is the peptide wherein R$_1$ is His, R$_2$ is Tyr, R$_3$ is D-Leu, R$_4$ is Leu and R$_5$ is NHCH$_2$—CH$_3$.

Other examples of the peptide compounds include LH-RH antagonists (see U.S. Pat. Nos. 4,086,219, 4,124,577, 4,253,997, 4,317,815). Examples thereof include N-(2S-tetrahydrofuroryl)Gly-3-(2-naphthyl)-D-alanyl-(4-chloro)-D-Phe-3-(3-pyridyl)-D-Ala-L-Ser-N-methyl-L-Tyr-(N-ε-nicotinyl)-D-Lys-L-Leu-(N-ε-isopropyl)-L-Lys-L-Pro-D-Ala•NH$_2$.

Other examples of the peptide compounds include GPIIb/IIIa antagonists, in particular, snake venom peptides having GPIIb/IIIa antagonism (e.g., barbourin), peptides having the sequence Arg-Gly-Asp such as Arg-Gly-Asp-Ser, (Arg-Gly-Asp-Ser)tetramer, Gly-Arg-Gly-Asp-Ser-Pro, cyclo-S,S-[Ac-Cys(N$^α$-methyl)Arg-Gly-D-Asn-penicillamine]—NH$_2$) (SK&F-106760); compounds having similar activity to GPIIb/IIIa antagonism, such as (S)-4-[(4-amidinobenzoyl)glycyl]-3-methoxy-carbonylmethyl-2-oxopiperazine-1-acetic acid, 4-(4-amidinobenzoylglycyl)-2-oxopiperazine-1,3-diacetic acid hydrochloride, 2-S-(n-butylsulfonylamino)-3-[4-(N-piperidin-4-yl) butyloxyphenyl]-propionic acid hydrochloride (MK-383), L-Tyr-N-(butyl-sulfonyl)-O-[4-(4-piperidinyl)butyl] monohydrochloride (L-700462), ethyl[4-[[4-(aminoiminomethyl)phenyl]amino]-1,4-dioxybutyl]amino-4-pentynoate (SC-56484), [1-[N-(p-amidinophenyl)-L-Tyr]-4-piperidinyl]acetic acid (Ro-44-9883), cyclic[D-2-aminobutyryl-N-2-methyl-L-Arg-Gly-L-Asp-3-aminomethyl-benzoic acid] methanesulfonate (DMP 728), etc.

Other examples of the peptide compounds include (S)-4-(4-guanidinobenzoylamino)acetyl-3-[3-(4-guanidinobenzoylamino)propyl]-2-oxopiperazine-1-acetic acid hydrochloride, and (S)-4-(4-amidinobenzoyl-amino) acetyl-3-[3-(4-amidinobenzoyl-amino)propyl]-2-oxopiperazine-1-acetic acid hydrochloride.

In addition, other examples of the peptide compounds include polypeptides such as insulin, somatostatin, and somatostatin derivatives represented, for example, by the formula (II):

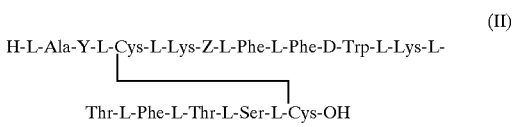

wherein Y is D-Ala, D-Ser or D-Val, Z is Asn or Ala, or salts thereof (see U.S. Pat. Nos. 4,087,390, 4,093,574, 4,100,117 and 4,253,998), growth hormone, prolactin, adrenocorticotropic hormone (ACTH), melanocyte-stimulating hormone (MSH), thyrotropin-releasing hormone (TRH) and salts thereof, and derivatives thereof represented, for example, by the formula (III):

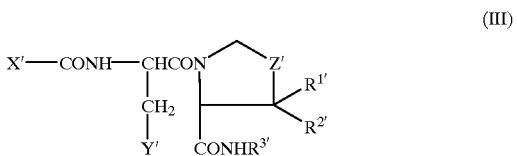

wherein X' is a 4-, 5- or 6-membered heterocyclic group (e.g., γ-butyrolactone-γ-carbonyl, L-pyroglutamyl, L-N-(2-oxopiperidin-6-yl-carbonyl), Y' is imidazol-4-yl or 4-hydroxyphenyl, Z' is CH$_2$ or S, R$^{1'}$ and R$^{2'}$ are the same or different and are hydrogen or a C$_{1-8}$ alkyl group (e.g., methyl, ethyl, propyl), R$^{3'}$ is hydrogen or an optionally substituted aralkyl group, or salts thereof (JP-A 50-121273, JP-A 52-116465), thyroid-stimulating hormone (TSH), luteinizing hormone (LH), follicle-stimulating hormone (FSH), parathyroid hormone (PTH) and derivatives thereof represented, for example, by the formula (VIII):

R$^{1''}$-Val-Ser-Glu-Leu-R$^{2''}$-His-Asn-R$^{3''}$-R$^{4''}$-R$^{5''}$-His-Leu-Asn-Ser-R$^{6''}$-R$^{7''}$-Arg-R$^{8''}$-Glu-R$^{9''}$-Leu-R$^{10''}$-R$^{11''}$-R$^{12''}$-Leu-Gln-Asp-Val-His-Asn-R$^{13''}$     (VIII)

wherein R$^{1''}$ is Ser or Aib, R$^{2''}$ is Met or a fat-soluble natural amino acid (e.g., Leu, Val, Trp), R$^{3''}$ is Leu, Ser, Lys or an aromatic amino acid (e.g., Tyr, Trp, Phe), R$^{4''}$ is Gly or a D-amino acid (e.g., D-Gly, D-Ala), R$^{5''}$ Lys or Leu, R$^{6''}$ is Met or a fat-soluble natural amino acid (e.g., Leu, Val, Trp), R$^{7''}$ is Glu or a basic amino acid (e.g., Lys, Arg), R$^{8''}$ is Val or a basic amino acid (e.g., Lys, Arg), R$^{9''}$ is Trp or 2-(1,3-dithiolan-2-yl)Trp, R$^{10''}$ is Arg or His, R$^{11''}$ is Lys or His, R$^{12''}$ is Lys, Gln or Leu, R$^{13''}$ is Phe or Phe-NH$_2$, or salts thereof (JP-A 5-32696, JP-A 4-247034, EP-A-510662, EP-A-477885, EP-A-539491), an N-terminal peptide fragment (1→34 position) of human PTH (hPTH(1→34)) (G. W. Tregear et al., Endocrinology, 93, 1349–1353 (1973)), vasopressin, vasopressin derivatives {e.g., desmopressin [Folia Endocrinologica Japonica, Vol. 54, No. 5, pp. 676–691 (1978)]}, oxytocin, calcitonin, calcitonin derivatives having similar activity to calcitonin represented by the formula (IV):

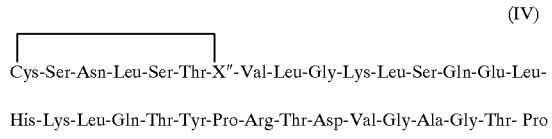

wherein X'' is 2-aminosuberic acid, or salts thereof (Endocrinology, 1992, 131/6 (2885–2890)), glucagon, gastrin, secretin, pancreozymin, cholecystokinin, angiotensin, human placental lactogen, human chorionic gonadotropin (HCG), enkephalin, enkephalin derivatives of the formula (V):

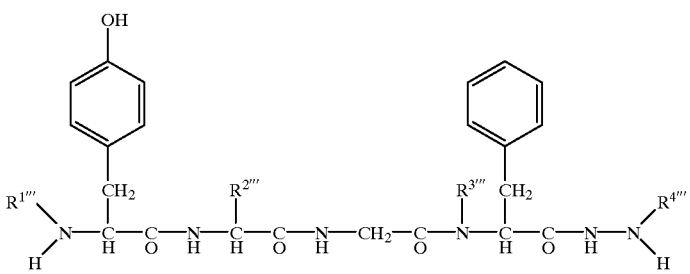

(V)

wherein $R^{1'''}$ and $R^{3'''}$ are hydrogen or a $C_{1-6}$ alkyl group (e.g., methyl, ethyl, propyl, butyl), $R^{2'''}$ is hydrogen or a D-α-amino acid (e.g., D-Ala, D-Ile), $R^{4'''}$ is hydrogen or an optionally substituted $C_{1-8}$ aliphatic acyl group (e.g., acetyl, propionyl, butyryl), or salts thereof (see U.S. Pat. No. 4,277,394 and EP-A-31,567), endorphin, kyotorphin, interferon (α-type, β-type, γ-type), interleukin (I, II, III, VI, XI, etc.), tuftsin, thymopoietin, thymosthymlin, thymic humoral factor (THF), serum thymic factor (FTS) and derivatives thereof of the formula (VI):

PGlu-X'''-Lys-Ser-Gln-Y'''-Z'''-Ser-Asn-OH    (VI)

wherein X''' is L- or D-Ala, Y''' and Z''' are Gly or a $C_{3-9}$ D-amino acid (e.g., D-Gly, D-Ala, D-Leu), or salts thereof (see U.S. Pat. No. 4,229,438) and other thymic factors [e.g., thymosin $α_1$ and $β_4$, thymic factor X, etc., Medicine in Progress, Vol. 125, No. 10, pp.835–843 (1983)], tumor necrosis factor (TNF), colony stimulating factor (CSF), motilin, dynorphin, bombesin, neurotensin, caerulein, bradykinin, urokinase, asparaginase, kallikrein, substance P, nerve growth factor, blood coagulation factors VIII and IX, lysozyme hydrochloride, polymyxin B, colistin, gramicidin, bacitracin, protein synthesis-stimulating peptide (G.B. Patent No. 8,232,082), gastric inhibitory polypeptide (GIP), vasoactive intestinal polypeptide (VIP), platelet-derived growth factor (PDGF), growth hormone-releasing factor (GRF, somatocrinin), bone morphogenetic protein (BMP), epidermal growth factor (EGF), erythropoietin (EPO), etc.

Other examples of the peptide compounds include endothelin antagonists such as cyclo-[D-α-aspartyl-3-[(4-phenylpiperazin-1-yl)carbonyl]-L-alanyl-L-α-aspartyl-D-2-(2-thienyl)glycyl-L-leucyl-D-tryptophyl] sodium salt, salts and derivatives thereof.

Examples of the antibiotics include gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cefalotin, cefaloridine, cefotiam, cefoxitin, cefsulodin, cefmenoxime, cefmetazole, cefazolin, cefotaxime, cefoperazone, ceftizoxime, moxolactam, thienamycin, sulfazecin, azusleonam, etc.

Examples of the antifungal agents include 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropyl)phenyl]-3(2H,4H)-1,2,4-triazolone, etc.

Examples of the antilipidemic agents include pravastatin, simvastatin, etc.

Examples of the drugs for circulatory systems include delapril hydrochloride, etc.

Examples of the anti-platelet aggregation agents include ticlopidine, cilostazol, alprostadil, limaprost, dipyridamole, ethyl icosapentaenoate, beraprost, ozagrel, aspirin, etc.

Examples of the antitumor agents include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U, poly ICLC, etc.

Examples of the antipyretics, analgesics and anti-inflammatory agents include sodium salicylate, sulpyrine, sodium flufenamate, diclofenac sodium, indomethacin sodium, morphine hydrochloride, pethidine hydrochloride, levorphanol tartarate, oxymorphone, etc.

Examples of the antitussive expectorants include ephedrine hydrochloride, methylephedrine hydrochloride, noscapine hydrochloride, codeine phosphate, dihydrocodeine phosphate, alloclamide hydrochloride, chlorphezianol hydrochloride, picoperidamine hydrochloride, cloperastine, protokylol hydrochloride, isoproterenol hydrochloride, salbutamol sulfate, terebutaline sulfate, etc.

Examples of the sedatives include chlorpromazine hydrochloride, prochlorperazine, trifluoperazine, atropine sulfate, methylscopolamine bromide, etc.

Examples of the muscle relaxants include pridinol methanesulfonate, tubocurarine chloride, pancuronium bromide, etc.

Examples of the antiepileptic agents include phenytoin sodium, ethosuximide, acetazolamide sodium, chlordiazepoxide hydrochloride, etc.

Examples of the antiulcer agents include metoclopramide, histidine hydrochloride, etc.

Examples of the antidepressants include imipramine, clomipramine, noxiptilin, phenelzine sulfate, etc.

Examples of the antiallergic agents include diphenhydramine hydrochloride, chlorpheniramine maleate, tripelennamine hydrochloride, methdilazine hydrochloride, clemizole hydrochloride, diphenylpyraline hydrochloride, methoxyphenamine hydrochloride, etc.

Examples of the cardiotonics include transbioxocamphor, theophyllol, aminophylline, etilefrine hydrochloride, etc.

Examples of the antiarrhythmic agents include propranolol hydrochloride, alprenolol hydrochloride, bufetolol hydrochloride, oxyprenolol hydrochloride, etc.

Examples of the vasodilators include oxyfedrine hydrochloride, diltiazem hydrochloride, tolazoline hydrochloride, hexobendine, bamethan sulfate, etc.

Examples of the hypotensive diuretics include hexamethonium bromide, pentolinium, mecamylamine hydrochloride, ecarazine hydrochloride, clonidine hydrochloride, etc.

Examples of the antidiabetic agents include glymidine sodium, glipizide, phenformin hydrochloride, buformin hydrochloride, metformin, etc.

Examples of the anticoagulants include heparin sodium, sodium citrate, etc.

Examples of the hemostatics include thromboplastin, thrombin, menadione sodium bisulfite, acetomenaphthone, ε-aminocaproic acid, tranexamic acid, carbazochrome sodium sulfonate, adrenochrome monoaminoguanidine methanesulfonate, etc.

Examples of the antituberculous agents include isoniazid, ethambutol, sodium para-aminosalicylate, etc.

Examples of the hormone preparations include prednisolone succinate, prednisolone sodium phosphate, dexamethasone sodium sulfate, betamethasone sodium phosphate, hexoestrol phosphate, hexoestrol acetate, methimazole, etc.

Examples of the narcotic antagonists include levallorphan tartrate, nalorphine hydrochloride, naloxone hydrochloride, etc.

Examples of the bone resorption inhibitors include (sulfur-containing alkyl)aminomethylenebisphosphonic acid, 4-phenoxybutylaminomethylene-1,1-bisphosphonate disodium salt, etc.

Examples of the angiogenesis inhibitors include angiostatic steroids [see Science, 221, 719 (1983)], fumagillin (see EP-A-325,199), fumagillol derivatives (e.g., O-monochloroacetylcarbamoylfumagillol, O-dichloroacetylcarbamoylfumagillol, etc. (see EP-A-357, 061, EP-A-359,036, EP-A-386,667, EP-A-415,294), etc.

The physiologically active substance may be distinct entity or in the form of any possible pharmaceutical salts thereof including particular salts described above. When the physiologically active substance has a basic group such as amino groups, it may form salts such as those with carbonic acid, hydrochloric acid, sulfuric acid, nitric acid, citric acid, maleic acid, tartaric acid, succinic acid, methanesulfonic acid, etc. When the physiologically active substance has an acidic group such as a carboxyl group, it may form salts such as those with alkaline metals (e.g., sodium, potassium, etc.), organic amines (e.g., triethylamine, etc.) or basic amino acids (e.g., arginine, etc.).

The amount of the water-soluble physiologically active substance to be used varies with factors related to the particular kind of physiologically active substance, desired pharmacological activity, duration time, etc. The concentration of the physiologically active substance in the solution of a polymer in an organic solvent is about 0.001 to 90% (W/W), preferably about 0.01 to 80% (w/W), more preferably about 0.01% to 70% (w/w).

The physiologically active substance is preferably used in the form of microparticles. The average particle size of the physiologically active substance is generally about 1 nm to about 10 μm, preferably about 1 nm to about 1 μm.

The polymer to be used in the present invention is a slightly water-soluble or water-insoluble polymer having biocompatibility. Examples of the polymers include biodegradable polymers such as poly fatty acid esters (e.g., polylactic acid, polyglycolic acid, polycitric acid, polymalic acid, polylactic acid caprolactone, etc.), poly-α-cyanoacrylic acid esters, poly-β-hydroxybutyric acid, poly-alkylene oxalates (e.g., polytrimethylene oxalate, polytetramethylene oxalate, etc.), poly ortho esters, poly ortho carbonates and other polycarbonates (e.g., polyethylene carbonate, polyethylene-propylene carbonate, etc.), polyamino acids (e.g., poly-γ-benzyl-L-glutamic acid, poly-L-alanine, poly-γ-methyl-L-glutamic acid, etc.), hyaluronic acid esters, etc. Other biocompatible copolymers include polystyrene, polymethacrylic acid, copolymer of acrylic acid and methacrylic acid, polyamino acids, dextran stearate, ethylcellulose, acetylcellulose, nitrocellulose, maleic anhydride copolymers, ethylene-vinylacetate copolymer, polyvinylacetate, polyacrylamide, etc.

These polymers may be used alone or in combination thereof. They may be used in the form of a copolymer or a mixture of these two or more polymers. They may also be in the form of salts thereof.

Among these polymers, biodegradable polymers are particularly preferred for injections. In the case of lactic acid/glycolic acid copolymer (PLGA), for example, the biodegradability (i.e., degradability in living bodies) is defined as the percentage (w/w) of water-soluble low-molecular weight fragments degraded from PLGA based on PLGA and it should be more than 10% in one year after subcutaneous or intramuscular administration, preferably more than 80% in three months after subcutaneous or intramuscular administration. The biodegradable polymer is preferably a polyester. Preferred examples of the biodegradable polymers include polymers or copolymers of hydroxycarboxylic acids or mixtures thereof.

The hydroxycarboxylic acids are not specifically limited, but preferably hydroxycarboxylic acids of the formula (VII):

(VII)

wherein R is hydrogen or an alkyl group.

Preferred examples of the alkyl groups represented by R in the above formula are straight-chain or branched alkyl groups having 1 to 8 carbon atoms, such as methyl, ethyl, propyl, isopropyl, butyl, isobutyl, tert-butyl, pentyl, hexyl, heptyl, octyl, etc. In particular, straight-chain or branched alkyl groups having 1 to 3 carbon atoms are preferred.

Preferred examples of the hydroxycarboxylic acids are glycolic acid, lactic acid, hydroxybutyric acid (e.g., 2-hydroxybutyric acid), 2'-hydroxyvaleric acid, 2-hydroxy-3-methylbutyric acid, 2-hydroxycaproic acid, 2-hydroxyisocaproic acid, 2-hydroxy-caprylic acid, etc. Glycolic acid, lactic acid, 2-hydroxybutyric acid, 2-hydroxy-3-methylbutyric acid and 2-hydroxycaproic acid are more preferred. In particular, glycolic acid, lactic acid and 2-hydroxybutyric acid are preferred. When these hydroxycarboxylic acids exist as D-isomers, L-isomers or racemic mixtures thereof, any one of them may be used. Preferably, racemic mixtures thereof are used.

The copolymers may be any of random, block and graft copolymers. The copolymer is preferably a glycolic acid copolymer that degrades in living bodies relatively rapidly and has a release period of not more than one month when used alone. In particular, lactic acid/glycolic acid copolymer and hydroxybutyric acid/glycolic acid copolymer are preferred.

The polymer to be used in the present invention can be synthesized by general synthetic methods as, for example, disclosed in JP-A 61-28521 without any problems.

In general, the weight-average molecular weight of the polymer to be used in the present invention is preferably about 2,000 to about 800,000, more preferably about 5,000 to about 200,000.

When lactic acid/glycolic acid copolymer is used as the above polymer, the molar ratio of lactic acid/glycolic acid is preferably 100/0 to 25/75, more preferably 100/0 to 50/50. The weight-average molecular weight of lactic acid/glycolic acid copolymer is preferably about 5,000 to about 30,000, more preferably about 5,000 to 20,000.

When hydroxybutyric acid/glycolic acid copolymer (e.g., 2-hydroxybutyric acid/glycolic acid copolymer) is used as the above polymer, the molar ratio of hydroxybutyric acid/ glycolic acid is preferably 100/0 to 25/75, more preferably 100/0 to 50/50. In particular, the molar ratio of 2-hydroxybutyric acid/glycolic acid is preferably about 60/40 to about 30/70. The weight-average molecular weight of hydroxybutyric acid/glycolic acid copolymer is preferably about 5,000 to about 25,000, more preferably about 5,000 to about 20,000.

When butyric acid/glycolic acid copolymer is used as the above polymer, the molar ratio of butyric acid/glycolic acid is preferably about 100/0 to 25/75.

When a mixture of polylactic acid (A) and glycolic acid/2-hydroxybutyric acid copolymer (B), for example, is used as the above polymer, the mixing ratio represented by (A)/(B) is in the range of about 10/90 to about 90/10 by weight, preferably about 25/75 to about 75/25 by weight. The weight-average molecular weight of polylactic acid is preferably about 5,000 to about 30,000, more preferably about 6,000 to about 20,000.

The molecular weight used herein means a molecular weight indicated as the molecular weight of polystyrene which is determined by gel permeation chromatography (GPC) using polystyrene as the standard material. The determination was carried out using GPC column KF 804L×2 (manufactured by Showadenko, Japan) and using chloroform as the mobile phase.

The polydispersity of the polymer is defined as the value of weight average molecular weight/number average molecular weight and it should be between 1 and 3.5, preferably between 1.5 and 2.5.

The amount of the polymer to be used depends upon the degree of the pharmacological activity, release rate and release period of the physiologically active substance, etc. For example, the polymer is used as the microcapsule base in an amount of about 0.2 to about 10,000 times by weight, preferably about 1 to about 1,000 times by weight, the weight of the physiologically active substance.

The concentration of the polymer in the oil phase is selected from the range of about 0.5% to about 90% (W/W), preferably about 2% to about 60% (W/w).

In order to inhibit the initial release of the physiologically active substance from the microcapsules, it is advantageous to add basic substances or oils and fats to the solution of a polymer in an organic solvent. The basic substances include, for example, basic amino acids such as L-arginine, N-methylglutamine, L-lysine, etc. In particular, L-arginine or N-methylglucamine is preferred. The oils and fats include, for example, vitamin E, intermediate fatty acids (e.g., miglyols), cholesterol, phospholipids, etc. The concentration of the basic substance in the solution of a polymer in an organic solvent is about 0.01% to about 20% (W/W), preferably about 0.1% to about 5% (W/W), more preferably about 0.1% to about 3% (W/W). The concentration of the oils and fats in the solution of a polymer in an organic solvent is about 0.01% to about 30% (W/W), preferably about 0.1% to about 20% (W/W), more preferably about 0.2% to about 10% (W/W).

In the present invention, the aqueous phase preferably also contains an osmotic pressure adjustor. Any osmotic pressure adjustor can be used so long as it produces osmotic pressure in an aqueous solution thereof.

Examples of the osmotic pressure adjustors include water-soluble polyhydric alcohols; water-soluble monohydric alcohols; water-soluble inorganic materials (e.g., inorganic salts); water-soluble monosaccharides, disaccharides, oligosaccharides and polysaccharides or their derivatives; water-soluble organic acids or salts thereof; water-soluble amino acids; water-soluble peptides, proteins or their derivatives; etc. Preferred examples thereof are water-soluble polyhydric alcohols; water-soluble inorganic acids; water-soluble monosaccharides, disaccharides, oligosaccharides and polysaccharides or their derivatives; and water-soluble organic acids and their salts. In particular, salts, water-soluble polyhydric alcohols and water-soluble inorganic acids are preferred.

Examples of the above water-soluble inorganic salts include alkaline metal halides such as potassium chloride, sodium chloride, potassium bromide, sodium bromide, potassium iodide, sodium iodide, etc.; alkaline earth metal halides such as calcium chloride, magnesium chloride, etc.; alkaline metal sulfates such as sodium sulfate, potassium sulfate, etc.; alkaline earth metal sulfates such as magnesium sulfate, calcium sulfate, etc.; alkaline metal phosphates such as potassium dihydrogenphosphate, dipotassium hydrogenphosphate, potassium phosphate, sodium dihydrogenphosphate, disodium hydrogenphosphate, sodium phosphate, etc. In particular, sodium chloride is preferred.

Examples of the above water-soluble polyhydric alcohols include dihydric alcohols (e.g., glycerin, etc.), pentahydric alcohols (e.g., arabitol, xylitol, adonitol, etc.), hexahydric alcohols (e.g., mannitol, sorbitol, etc.), etc. In particular, hexahydric alcohols are preferred.

Examples of the water-soluble monohydric alcohols include methanol, ethanol, isopropyl alcohol, etc. In particular, ethanol is preferred.

Examples of the above water-soluble monosaccharides include pentoses (e.g., arabinose, xylose, ribose, 2-deoxyribose, etc.) and hexoses (e.g., glucose, fructose, galactose, mannose, sorbose, rhamnose, fucose, etc.). In particular, hexoses are preferred.

Examples of the above water-soluble disaccharides include maltose, cellobiose, α-trehalose, lactose, sucrose, etc. In particular, lactose and sucrose are preferred.

Examples of the above water-soluble oligosaccharides include trisaccharides (e.g., maltotriose, raffinose, etc.) and tetrasaccharides (e.g., stachyose, etc.). In particular, trisaccharides are preferred.

Examples of the above water-soluble polysaccharides include glucans such as cellulose, starch, glycogen, etc., galacturonan such as pectic acid, etc., mannuronan such as alginic acid, etc., fructans such as inulin, levan, etc., N-acetylglycosamine polymers such as chitin, etc., xylans such as xylan of rice straw, etc., diheteroglucans such as mannan, glucomannan, galactomannan, hyaluronic acid, chondroitin sulfate, heparin, etc. In particular, glucans, and diheteroglucans are preferred.

Examples of the derivatives of the above water-soluble monosaccharides, disaccharides, oligosaccharides and polysaccharides include glucosamine, galactosamine, glucuronic acid, galacturonic acid, etc.

Examples of the above water-soluble organic acids or salts thereof include citric acid, tartaric acid, malic acid, alkaline metal (e.g., sodium, potassium, etc.) salts thereof, etc.

Examples of the above water-soluble amino acids include neutral amino acids such as glycine, alanine, valine, leucine, isoleucine, phenylalanine, tyrosine, tryptophan, serine, threonine, proline, hydroxyproline, cysteine, methionine, etc.; acidic amino acids such as aspartic acid, glutamic acid, etc.; basic amino acids such as lysine, arginine, histidine, etc. Salts of these water-soluble amino acids with acids (e.g., hydrochloric acid, sulfuric acid, phosphoric acid, etc.) or alkalis (e.g., alkaline metals such as sodium, potassium, etc.) can also be used.

Examples of the water-soluble peptides, proteins or their derivatives include casein, globulin, prolamin, albumin, gelatin, etc.

These osmotic pressure adjustors can be used alone or in combination thereof. When the osmotic pressure adjustor is a non-inonic material, the concentration of the osmotic pressure adjustor in the outer aqueous phase is about 0.001% to about 60% (W/W), preferably about 0.01 to about 40% (W/W), more preferably about 0.05 to about 30% (W/W). When the osmotic pressure adjustor is an ionic material, it is used in a concentration calculated by dividing the above concentration by the total ionic valency. The osmotic pressure adjustor may be added so that their concentration exceeds their solubility, and a part of it may be dispersed.

The microcapsules of the present invention can be prepared by an s/o/w type in-water drying process, for example, as follows.

Initially, an amorphous water-soluble physiologically active substance is dispersed in a solution of a polymer in a water-insoluble organic solvent, and the resulting dispersion is mixed well to obtain an s/o type emulsion. In the emulsion, the physiologically active substance is substantially homogeneously dispersed in the polymer solution.

If the water-soluble physiologically active substance is available in amorphous form, it can be used as it is. Even if it is available in crystalline form, however, it can be used after making it amorphous. The amorphous water-soluble physiologically active substance is preferably obtained from an aqueous solution, preferably a dilute aqueous solution, of a water-soluble physiologically active substance by a rapid drying process such as freeze drying or spray drying. As described above, the amorphous water-soluble physiologically active substance is preferably used in the form of microparticles, and the average particle size of the physiologically active substance is generally about 1 nm to about 10 $\mu$m, preferably about 1 nm to about 1 $\mu$m. If the physiologically active substance is available in the form of microparticles, it can be used as it is. If not, it can be used after pulverizing it to microparticles by conventional methods such as the jet mill method, atomization, or ball mill method.

The water-insoluble organic solvent is not specifically limited so long as it dissolves the polymer and is insoluble in water. Examples of the water-insoluble organic solvents include halogenated hydrocarbons (e.g., dichloromethane, chloroform, dichlorohexane, chloroethane, dichloroethane, trichloroethane, carbon tetrachloride, etc.), esters (e.g., ethyl acetate, etc.), ethers (e.g., ethyl ether, etc.), aromatic hydrocarbons (e.g., benzene, toluene, etc.), hydrocarbons (e.g., n-pentane, n-hexane, etc.), etc.

The emulsification of the above s/o type emulsions can be carried out by conventional dispersion techniques such as intermittent shaking, mixing by means of a mixer (e.g., propeller agitator, turbine agitator, etc.), colloid mill operation, mechanical homogenization, ultrasonication, etc. In this case, it is advantageous to use the above water-insoluble organic solvent in combination with a water-soluble organic solvent. The water-soluble organic solvent is not specifically limited so long as it is soluble in water and miscible with the above water-insoluble organic solvent.

Examples of the water-soluble organic solvents include alcohols (e.g., methanol, ethanol, propyl alcohol, isopropyl alcohol, etc.), acetone, acetonitrile, etc. In the s/o type emulsions, it is preferred that the physiologically active substance be dispersed in the form of fine microparticles having an average particle size of about 1 nm to about 10 $\mu$m, preferably about 1 nm to about 1 $\mu$m.

The s/o type emulsion thus prepared is subjected to in-water drying in an aqueous phase. Preferably, the aqueous phase contains an osmotic pressure adjustor in the concentration noted above. That is, the oil phase is added to the second phase (aqueous phase) to form an s/o/w type emulsion, followed by removal of the solvent in the oil phase to prepare microcapsules. The second phase (aqueous phase) may contain an emulsifying agent. Any emulsifying agent can be used so long as it generally forms stable o/w type emulsions. Examples thereof include anionic surfactants (e.g., sodium oleate, sodium stearate, sodium laurate, etc.); nonionic surfactants such as polyoxyethylenesorbitan fatty acid esters (e.g., TWEEN 60, TWEEN 80 (Atlas Powder Co.), etc.), polyoxyethylene castor oil derivatives (e.g., HCO-60, HCO-50 (Nikko Chemicals), etc.), polyvinyl pyrrolidone, polyvinyl alcohol, carboxymethyl cellulose, lecithin, gelatin, etc. These emulsifying agents can be used alone or in combination thereof. They are used in a concentration appropriately selected from the range of about 0.01% to about 20% (W/W), preferably about 0.05% to about 10% (W/W).

The solvent in the oil phase can be removed by conventional methods, for example, by stirring the emulsion with a propeller-type stirrer, magnetic stirrer, etc., under atmospheric pressure or gradually reduced pressure, or by evaporating the solvent while controlling the degree of vacuum by using a rotary evaporator, etc. In this case, when solidification of the polymer proceeds to some degree and the loss of the physiologically active substance caused by its release from the internal phase is decreased, the s/o/w type emulsion may be warmed gradually to remove the solvent completely. This operation shortens the removal time. Alternatively, when the polymer is thickened and solidified by methods other than those based on temperature, the solvent may be removed by merely allowing the s/o/w type emulsion to stand with stirring, or by warming the emulsion, or by spraying nitrogen gas, etc. This step of removing the solvent is important and greatly influences the surface structure of microcapsules that controls the release of the physiologically active substance. For example, rapid removal of the solvent produces many or larger pores on the surface, thereby increasing the release rate of the physiologically active substance.

The microcapsules thus obtained are collected by centrifugation or filtration. Then, the free physiologically active substance, carriers for the substance, etc., attached onto the surface of the microcapsules are washed off with distilled water repeatedly several times. Water and solvent in the microcapsules are completely dried under reduced pressure, if necessary, with warming.

The microcapsules thus obtained are screened, if necessary after light pulverization, to remove microcapsules which are too large. The microcapsule size varies with the desired degree of prolonged release. When the microcapsules are used as suspensions, the microcapsule size can be in the range which satisfies their dispersibility and needle pass requirements. For example, the average diameter is preferably in the range of about 0.5 to about 400 $\mu$m, more preferably about 2 to about 200 $\mu$m.

The microcapsules of the present invention can be administered as injections or implants intramuscularly, subcutaneously, or into blood vessels, organs, cava articulare or foci such as tumor. In addition, they can be administered after processing them to form various preparations. They can also be used as raw materials in the production of such preparations.

The above preparations include injections, oral preparations (e.g., powders, granules, capsules, tablets, etc.), nasal preparations, suppositories (e.g., rectal suppositories, vaginal suppositories, etc.), etc.

When the microcapsules of the present invention are processed into injections, the microcapsules are dispersed in an aqueous vehicle together with a dispersing agent (e.g., TWEEN 80, HCO-60 (manufactured by Nikko Chemicals), carboxymethylcellulose, sodium alginate, etc.), a preservative (e.g., methylparaben, propylparaben, benzyl alcohol, chlorobutanol, etc.), a tonicity agent (e.g., sodium chloride, glycerin, sorbitol, glucose, etc.), etc., to prepare aqueous suspensions. They may also be dispersed in a vegetable oil (e.g., olive oil, sesame oil, peanut oil, cottonseed oil, corn oil, etc.), propylene glycol, etc., to prepare oily suspensions. In this manner, sustained-release injections can be prepared.

In addition to the above components, excipients (e.g., mannitol, sorbitol, lactose, glucose, etc.) may be added to the above sustained-release microcapsule injections as suspensions. After redispersion, the injections are solidified by freeze drying or spray drying, and distilled water for injection or an appropriate disperser may be added just before use. In this manner, more stable sustained-release injections can be obtained.

The microcapsules of the present invention can be processed into tablets by conventional methods. For example, to the microcapsules are added an excipient (e.g., lactose, crystalline cellulose, sucrose, starch such as corn starch, etc.), a disintegrating agent (e.g., starch such as corn starch, croscarmellose sodium, carboxymethylstarch sodium, calcium carbonate, etc.), a binder (e.g., crystalline cellulose, acacia, dextrin, carboxymethylcellulose, polyvinyl pyrrolidone, hydroxypropylcellulose, etc.) or a lubricant (e.g., talc, magnesium stearate, polyethylene glycol 6000, etc.), etc. Then the mixture is compressed for shaping.

The microcapsules of the present invention can be processed into solid, semi-solid or liquid nasal preparations by conventional methods. For example, the solid nasal preparations can be prepared as powdery compositions from the mirocapsules as they are or together with an excipient (e.g., glucose, mannitol, starch, microcrystalline cellulose, etc.), thickener (e.g., natural gum, cellulose derivatives, polyacrylates, etc.), etc. The liquid nasal preparations can be prepared as oily or aqueous suspensions in substantially the same manner as in injections. The semi-solid nasal preparations are preferably aqueous or oily gels or ointments. In any case, pH adjustors (e.g., carbonic acid, phosphoric acid, citric acid, hydrochloric acid, sodium hydroxide, etc.), preservatives (e.g., p-hydroxybenzoic acid esters, chlorobutanol, benzalkonium chloride, etc.), etc., may be added.

The microcapsules of the present invention can be processed into oily or aqueous solid suppositories, semi-solid or liquid suppositories by per se known methods. The oleaginous bases for the above composition are not specifically limited so long as they do not dissolve the microcapsules. Examples thereof include higher fatty acid glycerides [e.g., cacao butter, Witepsol (Dynamit-Nobel, Germany), etc.], intermediate fatty acids [e.g., Miglyol (Dynamit-Nobel), etc.], vegetable oils (e.g., sesame oil, soybean oil, cottonseed oil, etc.), etc. The aqueous bases include, for example, polyethylene glycol and propylene glycol. The aqueous gels include, for example, natural gum, cellulose derivatives, vinyl polymers, polyacrylates, etc.

Because the microcapsule of the present invention releases a certain amount of physiologically active substances over a long period, it has low toxicity and exhibits stable efficacy. Thus, the microcapsule can be a safe and effective sustained-release preparation. For example, although GPIIb/IIIa antagonists have a bleeding tendency as a side effect, the microcapsule of the present invention can maintain nontoxic effective concentrations of the GPIIb/IIIa antagonists over a long period. Thus, the microcapsule of the present invention can safely be used for treating various diseases such as diseases in the circulatory system (e.g., thrombosis, transient cerebral ischemic attack, cerebral thrombosis (acute phase), chronic arterial obstruction, extremital arterial thrombosis, pulmonary thromboembolism, cardiac infarction, cerebral infarction, hypertension, hyperlipemia), ulcer, asthma, bacterial or fungal infections, tumor, inflammatory diseases, epilepsy, depression, allergic diseases, arrhythmia, diabetes, tuberculosis, osteoporosis, etc., in mammals such as mice, rats, horses, cattle, humans, etc., depending upon the pharmacological activity of the physiologically active substances. Preferably, the microcapsule of the present invention are used for treating diseases in the circulatory system, in particular thrombosis, transient cerebral ischemic attack, cerebral thrombosis, chronic arterial obstruction, extremital arterial thrombosis, pulmonary thromboembolism, cardiac infarction, or cerebral infarction, and for maintenance therapy after treatment of the infarctions.

The therapeutic dose of the microcapsules or their preparations of the present invention varies depending upon such factors as the kind and content of physiologically active substance as an active ingredient, dosage forms, duration of the release of the active ingredient, recipient animals, and purposes of treatment. It is, however, sufficient to ensure that the effective therapeutic dose of the active ingredient will be administered. For example, the unit dose for an adult (body weight: 50 kg) may be selected from the range of about 1 mg to about 10 g, preferably about 10 mg to about 2 g, calculated as the weight of the microcapsules. In the case of administration of the above injections, the volume of the suspension can be selected from the range of about 0.1 to about 5 ml, preferably about 0.5 to about 3 ml.

Thus, pharmaceutical compositions can be prepared as the microcapsules which comprises a physiologically active substance in an effective therapeutic amount that is larger than a conventional unit dose and a biocompatible polymer and which can achieve sustained-release of the physiologically active substance over a long period.

The microcapsules of the present invention have, for example, the following advantages:

(1) An amorphous water-soluble physiologically active substance can be entrapped into the microcapsules more efficiently than in conventional processes such as the coacervation phase separation process.

(2) The initial drug release after administration of the microcapsules can be reduced.

(3) Because the total dosage in preparations can be reduced by using the microcapsules containing high contents of physiologically active substances, pain or topical irritation, for example, at a subcutaneously administered site can be relieved.

The following examples further illustrate the present invention in detail but are not to be construed to limit the scope thereof. In the examples, all the percents (%) are indicated as weight/weight percents unless otherwise indicated.

EXAMPLE 1

Method A:

The anti-platelet aggregation agent (S)-4-[(4-amidinobenzoyl)glycyl]-3-methoxy-carbonylmethyl-2-oxopiperazine-1-acetic acid (abbreviated herein as Compound A) in amorphous form (450 mg) obtained by freeze drying was dispersed in a solution of lactic acid/glycolic acid copolymer (lactic acid/glycolic acid=75/25, average molecular weight calculated as polystyrene=10500) (4.05 g) in dichloromethane (4 ml). The drug in the dispersion was pulverized to microparticles using Polytron, a homogenizer manufactured by Kinematica, Switzerland. Then, s/o/w type emulsions were prepared using a homogenizer in 0.2 (w/v)% aqueous PVA (polyvinyl alcohol) solution (800 ml) containing 2.7 (w/v)% sodium chloride. Then, the emulsions were slowly stirred with a conventional propeller agitator for 3 hours. After dichloromethane vaporized from the microcapsules and the microcapsules hardened, the microcapsules were collected by centrifugation and at the same time washed with purified water. The collected microcapsules were freeze-dried for a day to obtain powdery microcapsules.

Method B:

Compound A in crystalline form (450 mg) was dispersed in the above solution of lactic acid/glycolic acid copolymer (4.05 g) in dichloromethane (4 ml), the drug in the dispersion having been pulverized to microparticles using Polytron homogenizer. Then, s/o/w type emulsions were prepared using a homogenizer in 0.2 (w/v)% PVA aqueous solution (800 ml) containing 2.7 (w/v)% sodium chloride. Thus, powdery microcapsules were obtained in the same manner as that described above.

Table 1 shows the properties of the microcapsules obtained by the above two methods. Compound A in amorphous form increased the drug entrapment.

TABLE 1

| Method | Drug | Content | Entrapment |
|---|---|---|---|
| A | Freeze-dried amorphous | 9.2% | 92% |
| B | Crystal | 3.6% | 36% |

EXAMPLE 2

Compound A in amorphous form (450 mg) obtained by freeze drying was dispersed in a solution of lactic acid/glycolic acid copolymer (lactic acid/glycolic acid=75/25, average molecular weight calculated as polystyrene=10500) (3.96 g) in dichloromethane (4 ml) in which L-arginine (90 mg) had been dissolved. The drug in the dispersion was pulverized to microparticles using Polytron homogenizer. Then, s/o/w type emulsions were prepared using a homogenizer in 0.2 (w/v)% aqueous PVA solution (800 ml) containing 2.7 (w/v)% sodium chloride. Then, the emulsions were slowly stirred with a conventional propeller agitator for 3 hours. After dichloromethane vaporized from the microcapsules and the microcapsules hardened, the microcapsules were collected by centrifugation and at the same time washed with purified water. The collected microcapsules were freeze-dried for a day to obtain powdery microcapsules.

Table 2 shows the properties of the microcapsules obtained by this method. The microcapsules obtained by this method had an increased drug entrapment.

TABLE 2

| Drug | Content | Entrapment |
|---|---|---|
| Freeze-dried amorphous | 9.4% | 94% |

EXAMPLE 3

Compound A in amorphous form (450 mg) obtained by freeze drying was dispersed in a solution of lactic acid/glycolic acid copolymer (lactic acid/glycolic acid=75/25, average molecular weight calculated as polystyrene=8400) (3.96 g) in dichloromethane (4 ml) in which L-arginine (90 mg) had been dissolved. The drug in the dispersion was pulverized to microparticles using Polytron homogenizer. Then, s/o/w type emulsions were prepared using a homogenizer in 0.2 (w/v)% PVA aqueous solution (800 ml) containing 2.7 (w/v)% sodium chloride. Then, the emulsions were slowly stirred with a conventional propeller agitator for 3 hours. After dichloromethane vaporized from the microcapsules and the microcapsules hardened, the microcapsules were collected by centrifugation and at the same time washed with purified water. The collected microcapsules were freeze-dried for a day to obtain powdery microcapsules.

The entrapment of the drug into the microcapsules obtained by this method was 98%.

EXAMPLE 4

Compound A in amorphous form (150 mg) obtained by spray drying was dispersed in a solution of lactic acid/glycolic acid copolymer (lactic acid/glycolic acid=50/50, average molecular weight calculated as polystyrene=8000) (4.26 g) in dichloromethane (4 ml) in which L-arginine (90 mg) had been dissolved. The drug in the dispersion was pulverized to microparticles using Polytron. Then, s/o/w type emulsions were prepared using a homogenizer in 0.2 (w/v)% PVA aqueous solution (800 ml) containing 0.9 (w/v)% sodium chloride. Then, the emulsions were slowly stirred with a conventional propeller agitator for 3 hours. After dichloromethane vaporized from the microcapsules and the microcapsules hardened, the microcapsules were collected by centrifugation and at the same time washed with purified water. The collected microcapsules were freeze-dried together with mannitol for a day to obtain powdery microcapsules.

EXAMPLE 5

Freeze-dried Compound A (300 mg) was dispersed in a solution of hydroxybutyric acid/glycolic acid copolymer (hydroxybutyric acid/glycolic acid=50/50, average molecular weight calculated as polystyrene=12000)(4.2 g) in dichloromethane (4 ml). The drug in the dispersion was pulverized to microparticles using Polytron homogenizer. Then, s/o/w type emulsions were prepared using a homogenizer in 0.2 (w/v)% PVA aqueous solution (1000 ml) containing 1.8 (w/v)% sodium chloride. Then, the emulsions were slowly stirred with a conventional propeller agitator for 3 hours. After dichloromethane vaporized from the microcapsules and the microcapsules hardened, the microcapsules were collected by centrifugation and at the same time washed with purified water. The collected microcapsules were freeze-dried together with mannitol for a day to obtain powdery microcapsules.

EXAMPLE 6

Microcapsules were prepared according to the same manner as that described in Example 1 except that the endotheline antagonist cyclo-[D-α-aspartyl-3-[(4-phenylpiperazin-1-yl)carbonyl]-L-alanyl-L-α-aspartyl-D-2-(2-thienyl)glycyl-L-leucyl-D-tryptophyl] sodium salt in amorphous form obtained by freeze drying and the endotheline antagonist in crystalline form were used instead of Compound A.

The entrapment of amorphous form of the drug into the microcapsules obtained by this method was about 100%.

EXAMPLE 7

Microcapsules were prepared in the same manner as that described in Example 1 except that the anti-platelet aggregation agent 4-(4-amidinobenzoylglycyl)-2-oxopiperazine-1,3-diacetic acid hydrochloride in amorphous form obtained by freeze drying and the anti-platelet aggregation agent in crystalline form were used instead of Compound A.

Table 3 shows the properties of the microcapsules obtained in this method.

The microcapsules containing amorphous form of the drug that were obtained by this method showed an entrapment of about 1.5 times that of the microcapsules containing crystalline form of the drug.

TABLE 3

| Drug | Entrapment |
| --- | --- |
| Freeze-dried amorphous | 65% |
| Crystal | 42% |

EXAMPLE 8

The GPIIb/IIIa antagonist (Arg-Gly-Asp-Ser)tetramer in amorphous form (200 mg) obtained by freeze drying was dispersed in a solution of lactic acid/glycolic acid copolymer (lactic acid/glycolic acid=90/10, average molecular weight calculated as polystyrene=12000)(3.7 g) in dichloromethane (4 ml) in which L-arginine (100 mg) had been dissolved. The drug in the dispersion was pulverized to microparticles using Polytron homogenizer. Then, s/o/w type emulsions were prepared using a homogenizer in 0.5 (w/v)% PVA aqueous solution (800 ml) containing 2.7 (w/v)% sodium chloride cooled to 15° C. Then, the emulsions were slowly stirred with a conventional propeller agitator for 3 hours. After dichloromethane vaporized and the microcapsules hardened, the microcapsules were collected by centrifugation and at the same time washed with purified water. The collected microcapsules were freeze-dried together with mannitol for a day to obtain powdery microcapsules.

EXAMPLE 9

The antibiotic cefoxitin sodium in amorphous form (150 mg) obtained by freeze drying was dispersed in a solution of hydroxybutyric acid/glycolic acid copolymer (hydroxybutyric acid/glycolic acid=75/25, average molecular weight calculated as polystyrene=14000)(4.7 g) in dichloromethane (4 ml) in which N-methylglucamine (150 mg) had been dissolved. The drug in the dispersion was pulverized to microparticles using Polytron homogenizer. Then, s/o/w type emulsions were prepared using a homogenizer in 0.2 (w/v)% PVA aqueous solution (800 ml) containing 15 (w/v)% mannitol cooled to 15° C. Then, the emulsions were slowly stirred with a conventional propeller agitator for 3 hours. After dichloromethane vaporized and the microcapsules hardened, the microcapsules were collected by centrifugation and at the same time washed with purified water. The collected microcapsules were freeze-dried together with mannitol for a day to obtain powdery microcapsules.

EXAMPLE 10

The bone resorption inhibitor 4-phenoxybutylaminomethylene-1,1-bisphosphonate disodium salt in amorphous form (200 mg) obtained by freeze drying was dispersed in a solution of lactic acid/glycolic acid copolymer (lactic acid/glycolic acid=90/10, average molecular weight calculated as polystyrene=8400)(3.7 g) in dichloromethane (4-ml) in which L-arginine (100 mg) had been dissolved. The drug in the dispersion was pulverized to microparticles using Polytron homogenizer. Then, s/o/w type emulsions were prepared using a homogenizer in 0.1 (w/v)% PVA aqueous solution (800 ml) containing 10 (w/v)% mannitol cooled to 15° C. Then, the emulsions were slowly stirred with a conventional propeller agitator for 3 hours. After dichloromethane vaporized and the microcapsules hardened, the microcapsules were collected by centrifugation and at the same time washed with purified water. The collected microcapsules were freeze-dried for a day to obtain powdery microcapsules.

TEST EXAMPLE 1

The microcapsules (20 mg/kg) obtained in Example 2 were subcutaneously administered to male SD rats weighing about 300 g. FIG. 1 shows the time-course changes of the plasma levels of Compound A. Effective blood levels (20–100 ng/ml) were maintained over 3 weeks after the administration.

What is claimed is:

1. A sustained-release microcapsule which is obtained by the steps comprising:

selecting a dispersion of an amorphous water-soluble pharmaceutical agent having a particle size of from 1 nm–10 μm in a solution of a polymer in an organic solvent, wherein said pharmaceutical agent is dispersed in an amount of from 0.001–90% (w/w) and said polymer has a wt. avg. molecular weight of from 2,000–800,000;

dispersing said dispersion of amorphous water-soluble pharmaceutical agent in an aqueous phase to prepare an s/o/w emulsion; and subjecting the s/o/w emulsion to in-water drying.

2. The microcapsule according to claim 1, wherein the concentration of the pharmaceutical agent in the solution of a polymer in an organic solvent is from about 0.01% to about 70% (W/W).

3. The microcapsule according to claim 1, wherein the solution of a polymer in an organic solvent additionally contains a basic substance.

4. The microcapsule according to claim 3, wherein the basic substance is a basic amino acid.

5. The microcapsule according to claim 3, wherein the basic substance is L-arginine.

6. The microcapsule according to claim 3, wherein the basic substance is N-methylglucamine.

7. The microcapsule according to claim 3, wherein the concentration of the basic substance in the solution of a polymer in an organic solvent is about 0.1% to about 3% (W/W).

8. The microcapsule according to claim 1, wherein the aqueous phase additionally contains an osmotic pressure adjustor.

9. The microcapsule according to claim 8, wherein the osmotic pressure adjustor is a salt.

10. The microcapsule according to claim 9, wherein the salt is sodium chloride.

11. The microcapsule according to claim 1, wherein the pharmaceutical agent is dispersed in the polymer.

12. The microcapsule according to claim 1, wherein the amorphous water-soluble pharmaceutical agent is obtained from an aqueous solution of a water-soluble pharmaceutical agent by a drying process.

13. The microcapsule according to claim 12, wherein the drying process is freeze drying or spray drying.

14. The microcapsule according to claim 1, wherein the pharmaceutical agent is readily soluble in water.

15. The microcapsule according to claim 1, wherein the water-solubility of the pharmaceutical agent is not less than about 1 g/100 ml at 20° C.

16. The microcapsule according to claim 1, wherein the water-solubility of the pharmaceutical agent is not less than about 5 g/100 ml at 20° C.

17. The microcapsule according to claim 1, wherein the average particle size of the pharmaceutical agent is not more than about 1 μm.

18. The microcapsule according to claim 1, wherein the pharmaceutical agent is an acidic or neutral substance.

19. The microcapsule according to claim 14, wherein the pharmaceutical agent is a peptide or its derivative.

20. The microcapsule according to claim 19, wherein the peptide or its derivative is selected from the group consisting of a compound having LH-RH activity, an LH-RH antagonist, a GPIIb/IIIa antagonist, a compound having similar activity to GPIIb/IIIa antagonism, insulin, somatostatin, a somatostatin derivative, growth hormone, prolactin, adrenocorticotropic hormone (ACTH), melanocyte-stimulating hormone (MSH), thyrotropin-releasing hormone (TRH) or a salt or derivative thereof, thyroid-stimulating hormone (TSH), luteinizing hormone (LH), follicle-stimulating hormone (FSH), parathyroid hormone (PTH) or a derivative thereof, an N-terminal peptide fragment (1–34 position) of human PTH, vasopressin, a vasopressin derivative, oxytocin, calcitonin, a calcitonin derivative having similar activity to calcitonin, glucagon, gastrin, secretin, pancreozymin, cholecystokinin, angiotensin, human placental lactogen, human chorionic gonadotropin (HCG), enkephalin, an enkephalin derivative, endorphin, kyotorphin, interferon, interleukin, tuftsin, thymopoietin, thymosthymlin, thymic humoral factor (THF), serum thymic factor (FTS), an FTS derivative, thymosin, thymic factor X, tumor necrosis factor (TNF), colony stimulating factor (CSF), motilin, dynorphin, bombesin, neurotensin, caerulein, bradykinin, urokinase, asparaginase, kallikrein, substance P, nerve growth factor, a blood coagulation factor, lysozyme hydrochloride, polymyxin B, colistin, gramicidin, bacitracin, protein synthesis-stimulating peptide, gastric inhibitory polypeptide (GIP), vasoactive intestinal polypeptide (VIP), platelet-derived growth factor (PDGF), growth hormone-releasing factor (GRF), bone morphogenetic protein (BMP), epidermal growth factor (EGF), erythropoietin (EPO), and an endothelin antagonist or a salt or derivative thereof.

21. The microcapsule according to claim 20, wherein the compound having LH-RH activity is a compound represented by the formula (I):

(Pyr)Glu-R$_1$-Trp-Ser-R$_2$-R$_3$-R$_4$-Arg-Pro-R$_5$     (I)

wherein R$_1$ is His, Tyr, Trp or p-NH$_2$-Phe; R$_2$ is Tyr or Phe; R$_3$ is Gly or a D-amino acid residue; R$_4$ is Leu, Ile or Nle; R$_5$ is Gly-NH-R$_6$ or NH-R$_6$ in which R$_6$ is H or lower alkyl optionally substituted with hydroxy, or a salts thereof.

22. The microcapsule according to claim 21, wherein R$_1$ is His, R$_2$ is Tyr, R$_3$ is D-Leu, R$_4$ is Leu, and R$_5$ is NHCH$_2$—CH$_3$.

23. The microcapsule according to claim 20, wherein the LH-RH antagonist is N-(2S-tetrahydrofuroryl)Gly-3-(2-naphthyl)-D-alanyl-(4-chloro)-D-Phe-3-(3-pyridyl)-D-Ala-L-Ser-N-methyl-L-Tyr-(N-ε-nicotinyl)-D-Lys-L-Leu-(N-ε-isopropyl)-L-Lys-L-Pro-D-Ala·NH$_2$.

24. The microcapsule according to claim 20, wherein the GPIIb/IIIa antagonist is barbourin, a peptide having the sequence Arg-Gly-Asp.

25. The microcapsule according to claim 24, wherein the peptide having the sequence Arg-Gly-Asp is a peptide selected from the group consisting of Arg-Gly-Asp-Ser, (Arg-Gly-Asp-Ser)tetramer, Gly-Arg-Gly-Asp-Ser-Pro, and cyclo-S,S-[Ac-Cys(N$^\alpha$-methyl)Arg-Gly-D-Asn-penicillamine]-NH$_2$).

26. The microcapsule according to claim 20, wherein the compound having similar activity to GPIIb/IIIa antagonism is selected from the group consisting of (S)-4-[(4-amidinobenzoyl)glycyl]-3-methoxy-carbonylmethyl-2-oxopiperazine-1-acetic acid, 4-(4-amidinobenzoylglycyl)-2-oxopiperazine-1,3-diacetic acid hydrochloride, 2-S-(n-butylsulfonyl-amino)-3-[4-(N-piperidin-4-yl)butyloxyphenyl]-propionic acid hydrochloride, L-Tyr-N-(butylsulfonyl)-O-[4-(4-piperidinyl)butyl] monohydrochloride, ethyl[4-[[4-(aminoiminomethyl)phenyl]amino]-1,4-dioxybutyl]amino-4-pentynoate, [1-[N-(p-amidinophenyl)-L-Tyr]-4-piperidinyl]acetic acid, and cyclic[D-2-aminobutyryl-N-2-methyl-L-Arg-Gly-L-Asp-3-aminomethyl-benzoic acid] methanesulfonate.

27. The microcapsule according to claim 20, wherein the endothelin antagonist is cyclo-[D-α-aspartyl-3-[(4-phenylpiperazin-1-yl)carbonyl]-L-alanyl-L-α-aspartyl-D-2-(2-thienyl)glycyl-L-leucyl-D-tryptophyl] sodium salt.

28. The microcapsule according to claim 12, wherein the peptide or its derivative is (S)-4-[(4-amidinobenzoyl)glycyl]-3-methoxy-carbonylmethyl-2-oxopiperazine-1-acetic acid].

29. The microcapsule according to claim 1, wherein the polymer is a biodegradable polymer.

30. The microcapsule according to claim 29, wherein the biodegradable polymer is a polyester.

31. The microcapsule according to claim 30, wherein the polyester is lactic acid/glycolic acid copolymer.

32. The microcapsule according to claim 31, wherein the molar ratio of lactic acid/glycolic acid is 100/0 to 25/75.

33. The microcapsule according to claim 32, wherein the molar ratio of lactic acid/glycolic acid is 100/0 to 50/50.

34. The microcapsule according to claim 31, wherein the weight-average molecular weight of lactic acid/glycolic acid copolymer is about 5,000 to about 30,000.

35. The microcapsule according to claim 31, wherein the weight-average molecular weight of lactic acid/glycolic acid copolymer is about 5,000 to about 20,000.

36. The microcapsule according to claim 30, wherein the polyester is hydroxybutyric acid/glycolic acid copolymer.

37. The microcapsule according to claim 36, wherein the molar ratio of hydroxybutyric acid/glycolic acid is 100/0 to 25/75.

38. The microcapsule according to claim 37, wherein the molar ratio of hydroxybutyric acid/glycolic acid is 100/0 to 50/50.

39. The microcapsule according to claim 36, wherein the weight-average molecular weight of hydroxybutyric acid/glycolic acid copolymer is about 5,000 to about 25,000.

40. The microcapsule according to claim 39, wherein the weight-average molecular weight of hydroxybutyric acid/glycolic acid copolymer is about 5,000 to about 20,000.

41. The microcapsule according to claim 1, which is for treating a disease in the circulatory system.

42. The microcapsule according to claim 1, which is for treating thrombosis.

* * * * *